United States Patent

Waldeck et al.

[11] Patent Number: 5,952,327
[45] Date of Patent: Sep. 14, 1999

[54] PHOSPHONIC ACID-SUBSTITUTED BENZAZEPINONE-N-ACETIC ACID DERIVATIVES PROCESS FOR THEIR PREPARATION AND PHARMACEUTICAL COMPOSITIONS COMPRISING THEM

[75] Inventors: Harald Waldeck, Isernhagen; Joerg Meil, Barsinghausen; Dirk Thormaehlen, Rheden; Michael Wurl, Schloss Ricklingen, all of Germany

[73] Assignee: Solvay Pharmaceuticals GmbH, Hannover, Germany

[21] Appl. No.: 09/189,796

[22] Filed: Nov. 12, 1998

[30] Foreign Application Priority Data

Nov. 12, 1997 [DE] Germany ............ 197 50 002

[51] Int. Cl.[6] ................. A61K 31/55; C07D 223/16; C07D 223/32
[52] U.S. Cl. ......................... 514/213; 540/487
[58] Field of Search ............... 514/213; 540/487

[56] References Cited

U.S. PATENT DOCUMENTS 5,677,297  10/1997  Waldeck et al. ............ 514/211

FOREIGN PATENT DOCUMENTS 733 642 A1  9/1996  European Pat. Off. .
743 319 A1  11/1996  European Pat. Off. .
747 392 A1  12/1996  European Pat. Off. .

*Primary Examiner*—Mukund J. Shah
*Assistant Examiner*—Bruck Kifle
*Attorney, Agent, or Firm*—Evenson, McKeown, Edwards, & Lenahan, P.L.L.C.

[57] ABSTRACT

Compounds having NEP-inhibitory activity, corresponding to the formula I

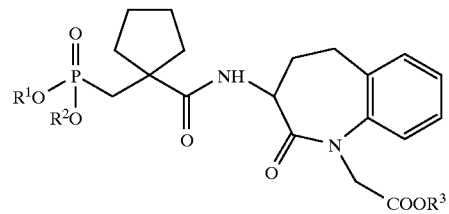

in which
  $R^1$ is hydrogen or a group forming a biolabile phosphonic acid ester,
  $R^2$ is hydrogen or a group forming a biolabile phosphonic acid ester and
  $R^3$ is hydrogen or a group forming a biolabile carboxylic acid ester
and physiologically acceptable salts of acids of formula I, and pharmaceutical compositions comprising these compounds.

4 Claims, No Drawings

PHOSPHONIC ACID-SUBSTITUTED BENZAZEPINONE-N-ACETIC ACID DERIVATIVES PROCESS FOR THEIR PREPARATION AND PHARMACEUTICAL COMPOSITIONS COMPRISING THEM

BACKGROUND OF THE INVENTION

The present invention relates to novel benzazepinone-N-acetic acid derivatives which are substituted in the 3-position by a cyclopentylcarbonylamino radical carrying a methylphosphonic acid radical in the 1-position, and their salts and biolabile esters, to pharmaceutical compositions comprising these compounds and to processes for the preparation of these compounds.

Published European Patent Application No. EP 733,642 discloses benzazepine-, benzoxazepine- and benzodiazepine-N-acetic acid derivatives which exert an inhibitory action on neutral endopeptidase (=NEP).

SUMMARY OF THE INVENTION

The object of the invention is to provide novel pharmaceutically active compounds having NEP-inhibitory activity with an activity profile which is favorable for the treatment of cardiac insufficiency and high blood pressure.

It has now been found that the novel benzazepinone-N-acetic acid derivatives according to the invention, which are substituted in the 3-position of the benzazepinone structure by a cyclopentylcarbonylamino radical carrying a methylphosphonic acid radical in the 1-position, have valuable cardioactive pharmacological properties and are distinguished by an activity profile which is favorable for the treatment of cardiovascular disorders, in particular cardiac insufficiency, and which is characterized by a combination of a marked inhibitory action on neutral endopeptidase with an inhibitory action on endothelin-converting enzyme (=ECE) and a good tolerability.

The invention relates to novel compounds of the general formula I

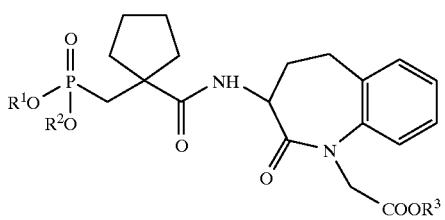

in which
$R^1$ is hydrogen or a group forming a biolabile phosphonic acid ester,
$R^2$ is hydrogen or a group forming a biolabile phosphonic acid ester and
$R^3$ is hydrogen or a group forming a biolabile carboxylic acid ester
and physiologically acceptable salts of acids of formula I, and processes for the preparation of these compounds and pharmaceutical compositions comprising these compounds.

The compounds of formula I are acid derivatives comprising carboxylic acid and phosphonic acid groups which are optionally esterified by groups forming biolabile esters. The biolabile esters of formula I are prodrugs of the free acids. Depending on the form of administration, the biolabile esters or the acids are preferred, the latter being particularly suitable for i.v. administration.

Suitable groups $R^1$ and $R^2$ for forming biolabile phosphonic acid esters include those which can be removed under physiological conditions in vivo with release of the respective phosphonic acid function. For example, groups which are suitable for this purpose include lower alkyl groups, $C_2$–$C_6$-alkanoyloxymethyl groups optionally substituted on the oxymethyl group by lower alkyl, or phenyl or phenyl-lower alkyl groups whose phenyl ring is optionally mono- or polysubstituted by lower alkyl, lower alkoxy or by a lower alkylene chain bonded to two adjacent carbon atoms. If the group $R^1$ and/or $R^2$ forming a biolabile ester is or contains lower alkyl, this may be branched or unbranched and may contain 1 to 4 carbon atoms. If $R^1$ and/or $R^2$ is an optionally substituted alkanoyloxymethyl group, it may contain a preferably branched alkanoyloxy group having 2 to 6, preferably 3 to 5, carbon atoms and may, for example, be a pivaloyloxymethyl radical (=tert-butylcarbonyloxymethyl radical). If $R^1$ and/or $R^2$ is an optionally substituted phenyl-lower alkyl group, this may contain an alkylene chain having 1 to 3, preferably 1, carbon atoms. If the phenyl ring is substituted by a lower alkylene chain, this may contain 3 to 4, in particular 3, carbon atoms and the substituted phenyl ring is in particular indanyl.

Suitable groups $R^3$ forming biolabile carboxylic acid esters are those which can be cleaved under physiological conditions in vivo with release of the carboxylic acid. For example, groups suitable for this purpose include lower alkyl groups, phenyl or phenyl-lower alkyl groups optionally mono- or polysubstituted in the phenyl ring by lower alkyl or lower alkoxy or by a lower alkylene chain bonded to two adjacent carbon atoms, dioxolanylmethyl groups optionally substituted in the dioxolane ring by lower alkyl or $C_2$–$C_6$-alkanoyloxymethyl groups optionally substituted on the oxymethyl group by lower alkyl. If the group $R^3$ forming a biolabile ester is or contains lower alkyl, this may be branched or unbranched and may contain 1 to 4 carbon atoms. If the group forming a biolabile ester is an optionally substituted phenyl-lower alkyl group, this may contain an alkylene chain having 1 to 3, preferably 1, carbon atom(s) and is preferably benzyl. If the phenyl ring is substituted by a lower alkylene chain, this may contain 3 to 4, preferably 3, carbon atoms. If $R^3$ is an optionally substituted alkanoyloxymethyl group, this may contain a preferably branched alkanoyloxy group having 2 to 6, preferably 3 to 5, carbon atoms and may be, for example, a pivaloyloxymethyl radical.

According to the invention, the novel compounds of formula I and their salts are obtained in that, in a manner known per se a) for the preparation of compounds of the general formula IV

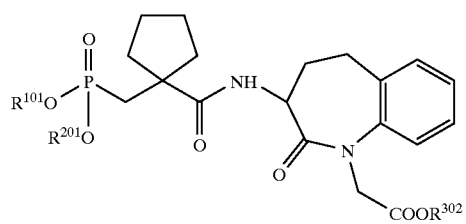

in which $R^{101}$ and $R^{201}$ independently of one another are each hydrogen or a phosphonic acid protective group and $R^{302}$ is a carboxylic acid protective group, compounds of the general formula II

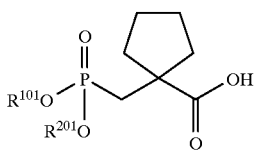

in which $R^{101}$ and $R^{201}$ have the above meanings, are reacted with compounds of the general formula III

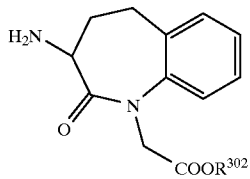

in which $R^{302}$ has the above meaning, and, if $R^{101}$ and/or $R^{201}$ are hydrogen, the free phosphonic acid function(s) is/are converted, if desired, into a biolabile phosphonic acid ester group by esterification with a compound of the general formula Va and/or Vb $$R^{101}\text{-}Y \qquad \text{(Va)}$$
$$R^{210}\text{-}Y \qquad \text{(Vb)}$$

in which $R^{110}$ and $R^{210}$ are each a group forming a biolabile phosphonic acid ester and Y is hydroxyl or a removable leaving group, and b) if in the compounds of formula IV the protective groups $R^{101}$, $R^{201}$ and/or $R^{302}$ are not desired groups forming a biolabile ester, these are successively removed simultaneously or individually in any desired sequence and, if desired, the acid functions liberated in each case are converted into biolabile ester groups by esterifying free phosphonic acid functions with a compound of the formula Va or Vb and/or esterifying the free carboxylic acid function with a compound of the general formula Vc $$R^{310}\text{-}Y \qquad \text{(Vc)}$$

in which $R^{310}$ is a group forming a biolabile carboxylic acid ester and Y has the above meaning,
and, if desired, acids of formula I are converted into their physiologically tolerable salts or salts of the acids of formula I are converted into the free compounds.

Suitable physiologically acceptable salts of acids of formula I include the respective alkali metal, alkaline earth metal or ammonium salts, for example their sodium, potassium or calcium salts or salts with physiologically acceptable, pharmacologically neutral organic amines such as, for example, diethylamine, tert-butylamine or phenyl-lower alkylamines such as α-methylbenzylamine.

Suitable phosphonic acid protective groups $R^{101}$ and $R^{201}$ include the customary protective groups for protecting phosphonic acid functions, which are then removed again by known methods. Suitable carboxylic acid protective groups $R^{302}$ include the customary protective groups for protecting carboxylic acid functions, which can then be removed again by known methods. Suitable protective groups for carboxylic acids are known, for example, from McOmie, "Protective Groups in Organic Chemistry", Plenum Press and Green, Wuts, "Protective Groups in Organic Synthesis", Wiley Interscience Publication. Suitable protective groups for phosphonic acids are known, for example, from Houben-Weyl "Methoden der Organischen Chemie" [Methods of Organic Chemistry] G. Thieme Verlag Stuttgart, New York 1982, pages 313–341 and from M. Kluba, A. Zwierak "Synthesis" 1978, pages 134–137 and from McOmie, "Protective Groups in Organic Chemistry", Plenum Press. Acid protective groups which can be employed are also groups forming a biolabile ester. The compounds of formula IV obtained in the reaction of compounds of formula II with compounds of formula III are in these cases already esters of formula I according to the invention.

According to the invention, suitable phosphonic acid protective groups $R^{101}$ and $R^{201}$ include groups which can be selectively removed or selectively introduced by suitable methods independently of one another and independently of a carboxylic acid protective group $R^{302}$ which is, for example, still present in the molecule. As a rule, phosphonic acid protective groups can easily be removed selectively in the presence of carboxylic acid protective groups by means of trimethylsilyl bromide. Examples of phosphonic acid protective groups removable under different conditions, which may be mentioned (and which can also be groups which form biolabile phosphonic acid esters) include: unbranched lower alkyl groups such as ethyl, which can easily be removed, for example, by acids such as trifluoroacetic acid, where, if both phosphonic acid functions are esterified with lower unbranched alkyl groups, only one of these alkyl groups can be removed under basic conditions; branched lower alkyl groups such as tert-butyl, which can easily be removed under acetic conditions, for example under the action of trifluoroacetic acid; phenylmethyl groups optionally substituted in the phenyl ring, such as benzyl, which can easily be removed by hydrogenolysis; alkanoyloxymethyl groups such as pivaloyloxymethyl, which can easily be removed, for example, by acids such as trifluoroacetic acid; and phenylmethyl groups mono- or polysubstituted in the phenyl ring by lower alkoxy, such as p-methoxybenzyl, which can be removed relatively easily under oxidative conditions, for example under the action of 2,3-dichloro-5,6-dicyano-1,4-benzoquinone (=DDQ) or cerium ammonium nitrite (=CAN).

Suitable carboxylic acid protective groups $R^{302}$ include those groups which can be selectively removed or selectively introduced independently of phosphonic acid protective groups possibly still present in the molecule. Examples of carboxylic acid protective groups removable under different conditions which may be mentioned (and which also may be groups which form biolabile carboxylic acid esters) include: unbranched lower alkyl groups such as ethyl, which can be removed comparatively easily under basic conditions; branched lower alkyl groups such as tert-butyl, which can easily be removed by acids such as trifluoroacetic acid; and phenylmethyl groups optionally substituted in the phenyl ring, such as benzyl, which can easily be removed hydrogenolytically or alternatively under basic conditions. Phenylmethyl groups mono- or polysubstituted in the phenyl ring by lower alkoxy, such as p-methoxybenzyl, which can be removed relatively easily under oxidative conditions, for example under the action of DDQ or CAN.

The compounds of formula I contain an asymmetric or chiral carbon atom, namely the carbon atom carrying the amide side chain in the 3-position of the benzazepine structure. The compounds can thus exist in two optically active stereoisomeric forms or as a racemate. The present invention includes both the isomerically pure compounds of formula I and the racemic mixtures. If $R^1$ and $R^2$ in compounds of formula I are not hydrogen and in each case have different meanings, the phosphorus atom of the phosphonic acid group can also be chiral. The invention also relates to the isomer mixtures and isomerically pure compounds of formula I formed as a result of chiral phosphorus atoms.

The reaction of the acids of formula II with the amines of formula III to give the amides of formula IV can be carried out by customary methods for forming amide groups by aminoacylation. Acylating agents which can be employed include the carboxylic acids of formula II or their reactive derivatives. Suitable reactive derivatives include in particular mixed acid anhydrides and acid halides. Thus it is possible, for example, to employ acid chlorides or acid bromides of the acids of formula II or mixed esters of the acids of formula II with organic sulfonic acids, for example with lower alkanesulfonic acids optionally substituted by halogen, such as methanesulfonic acid or trifluoromethanesulfonic acid, or with aromatic sulfonic acids such as, for example, benzenesulfonic acids or with benzenesulfonic acids substituted by lower alkyl or halogen, e.g. toluenesulfonic acids or bromobenzenesulfonic acids. The acylation can be carried out in an organic solvent which is inert under the reaction conditions at temperatures between −20° C. and room temperature. Suitable solvents include halogenated hydrocarbons such as dichloromethane or aromatic hydrocarbons such as benzene or toluene or cyclic ethers such as tetrahydrofuran (=THF) or dioxane or mixtures of these solvents.

The acylation can advantageously be carried out in the presence of an acid-binding reagent, in particular if a mixed anhydride of the acids of formula II with a sulfonic acid is used as an acylating agent. Suitable acid-binding agents include, for example, organic bases which are soluble in the reaction mixture, such as tertiary nitrogen bases, for example tert-lower-alkylamines and pyridines such as, for example, triethylamine, tripropylamine, N-methylmorpholine, pyridine, 4-dimethylaminopyridine, 4-diethylaminopyridine or 4-pyrrolidinopyridine. Organic bases employed in excess can simultaneously also serve as solvents.

If the acids of formula II themselves are employed as acylating agents, the reaction of the amino compounds of formula III with the carboxylic acids of formula II can advantageously also be carried out in the presence of a coupling reagent known from peptide chemistry as suitable for amide formation. Examples of coupling reagents which may be mentioned which promote amide formation with the free acids in that they react with the acid in situ with formation of a reactive acid derivative include: alkylcarbodiimides, e.g. cycloakylcarbodiimides such as dicyclohexylcarbodiimide or N-(3-dimethylaminopropyl)-N'-ethylcarbodiimide, carbonyldiimidazole and N-lower alkyl-2-halopyridinium salts, in particular halides or toluenesulfonates. The reaction in the presence of a coupling reagent can advantageously be carried out at temperatures from −30° to +50° C. in solvents such as halogenated hydrocarbons and/or aromatic solvents and optionally in the presence of an acid-binding amine described above.

The protective groups $R^{101}$, $R^{201}$ and $R^{302}$, if they are not desired groups forming a biolabile ester, can be removed in a known manner from the compounds of formula IV obtained by reaction of the compounds of formula II with the compounds of formula III.

If compounds of formula I are to be prepared in which $R^1$, $R^2$ and $R^3$ are identical groups forming a biolabile ester, advantageously identical protective groups are already selected in the starting compounds of formula II and in the starting compounds of formula III. In this case, protective groups can advantageously be selected which are simultaneously groups which form biolabile esters. If free acids of formula I are to be prepared in which $R^1$, $R^2$ and $R^3$ are each hydrogen, groups in each case removable under the same conditions, preferably under hydrogenolytic conditions, can be selected as protective groups $R^{101}$, $R^{201}$ and $R^{302}$. For example, for $R^{101}$, $R^{201}$ and $R^{302}$ benzyl groups can in each case be selected which are simultaneously cleaved under the conditions of a catalytic hydrogenation to give the free acid groups. Catalysts which can be used for the catalytic hydrogenation include, for example, noble metal catalysts such as palladium on active carbon. The reaction can be carried out in a solvent which is inert under the reaction conditions, for example a lower alcohol such as ethanol or a lower alkyl ester such as ethyl acetate, or in mixtures of these solvents. The catalytic hydrogenation is advantageously carried out at a hydrogen pressure of from 2 to 6 bar and at room temperature.

If free phosphonic acid groups and/or free carboxylic acid groups of compounds of formula I are to be esterified, for this purpose free phosphonic acid groups of compounds of formula I can be reacted in a known manner with compounds of formula Va or Vb. Free carboxylic acid groups of compounds of formula I can be reacted in a known manner with compounds of formula Vc. Suitable leaving groups Y in compounds of formulas Va, Vb and Vc include, for example, halogen, in particular chlorine or bromine, or radicals of lower alkanesulfonic acids such as, for example, trifluoromethanesulfonyloxy, or of aromatic sulfonic acids such as of benzenesulfonic acids, or of benzenesulfonic acids substituted by lower alkyl or halogen, such as toluenesulfonic acids.

If compounds of formula I are to be prepared in which $R^1$ and $R^2$ are each the same, but have a meaning other than $R^3$, starting compounds of formula II are advantageously used in which $R^{101}$ and $R^{201}$ have identical meanings and starting compounds of formula III in which $R^{302}$ has a meaning other than $R^{101}$ and $R^{201}$. For example, phosphonic acid protective groups $R^{101}$ and $R^{201}$ which are stable under hydrogenolytic conditions can be selected, such as lower alkyl, preferably ethyl. A group which is removable under hydrogenolytic conditions can simultaneously be used as a carboxylic acid protective group $R^{302}$. Under the conditions of a catalytic hydrogenation, only the benzyl group $R^{302}$ is cleaved to give the free carboxylic acid in compounds of formula IV obtained, while the ethyl groups $R^{101}$ and $R^{201}$ are retained. If desired, the free carboxylic acid can then be esterified with a compound of formula Vc. Likewise, in compounds of formula I in which the phosphonic acid protective groups $R^{101}$ and $R^{201}$ are groups which are stable under hydrogenolytic conditions, such as lower alkyl groups, preferably ethyl, and $R^{302}$ is a hydrogenolytically removable group such as the benzyl group, the ethyl groups $R^{101}$ and $R^{201}$ are first removed under acidic conditions, the benzyl group $R^{302}$ being retained. If desired, the free phosphonic acid groups can then be esterified with compounds of formula Va or Vb, for example with pivaloyloxymethyl chloride. The benzyl group $R^{302}$ removable under hydrogenolytic conditions can then be removed by catalytic reduction with hydrogen under known conditions in order to obtain compounds of formula I in which $R^3$ is hydrogen.

If compounds of formula I are desired in which $R^1$ and $R^2$ have different meanings, starting compounds of formula II can advantageously be used in which $R^{101}$ and $R^{201}$ have different meanings. For example, compounds of formula II can be selected as starting compounds in which $R^{101}$ is hydrogen and $R^{201}$ is a phosphonic acid protective group stable under hydrogenolytic conditions. For example, $R^{201}$ can be lower alkyl, preferably ethyl. If desired, the resulting compounds of formula I, in which $R^{101}$ is hydrogen, can subsequently also be reacted with suitable compounds of formula Va in order to obtain compounds of formula I in which $R^1$ and $R^2$ are groups forming different biolabile esters. The starting compounds of formula II in which $R^{101}$ is hydrogen can be obtained, for example, from compounds of formula II in which $R^{101}$ is a group removable under hydrogenolytic conditions, such as benzyl, by catalytic hydrogenation under known conditions.

In the reactions described above, the chiral carbon atoms in the starting compounds of formula III are not changed, so that, depending on the nature of the starting compounds, isomerically pure compounds of formula I or isomer mixtures can be obtained. In order to prepare stereochemically homogeneous compounds of formula I, stereochemically homogeneous compounds of formula II are advantageously reacted with stereochemically homogeneous compounds of formula III. If a compound of formula II which does not contain a chiral phosphorus atom is reacted with a racemic compound of formula III, a mixture of two enantiomers of the compound of formula I is obtained. If desired, the enantiomer mixture can be separated in a known manner, for example by chromatographic separation on chiral separating materials or by reaction of a free carboxylic acid of formula I with suitable optically active bases, for example (-)-α-methylbenzylamine, and subsequent resolution of the optical antipodes by fractional crystallization of the resulting salts.

The starting compounds of formula II can be obtained by known methods. Thus compounds of formula II, for example, can be obtained by reacting compounds of the general formula VI

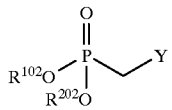

in which $R^{102}$ and $R^{202}$ are each phosphonic acid protective groups and Y has the above meaning, with a cyclopentanecarboxylic acid of formula VII

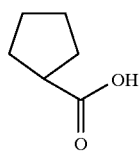

and, if desired, then removing the protective groups $R^{102}$ and/or $R^{202}$ again in a known manner. For example, compounds of formula VI can be employed in which Y is the radical of a lower alkanesulfonic acid, preferably trifluoromethanesulfonyloxy.

The reaction can be carried out in a known manner under the conditions of a nucleophilic substitution in an organic solvent which is inert under the reaction conditions by reaction of the cyclopentanecarboxylic acid with a strong base capable of forming the dianion of the cyclopentanecarboxylic acid and subsequent reaction with the phosphonic acid ester derivative of formula VI. Suitable solvents include, for example, open-chain dialkyl ethers such as diethyl ether or cyclic ethers such as tetrahydrofuran (THF). Suitable strong bases include, for example, non-nucleophilic organic alkali metal amides such as lithium diisopropylamide (=LDA). The cyclopentanecarboxylic acid is advantageously reacted in THF with two equivalents of LDA, and the reaction mixture is then reacted further with a compound of formula VI. The reaction temperature can be between -70° and 0° C.

Compounds of formula VI can be obtained in a known manner, for example by reacting the phosphonic acid diesters of the general formula VIII

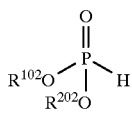

in which $R^{102}$ and $R^{202}$ have the above meanings, with a source of formaldehyde, for example with paraformaldehyde. The reaction can advantageously be carried out under solvent-free conditions and with involvement of bases which are soluble in the reaction mixture. The bases used can be the non-nucleophilic bases described above for the reaction of compounds of formula II with compounds of formula III. The reaction can advantageously be carried out at temperatures between 50° and 130° C., preferably between 80° and 120° C. If desired, the resulting compounds of formula VI in which Y is hydroxyl, can then be converted in a known manner into compounds of formula VI, in which Y is a removable leaving group.

Compounds of formula VIII are known or can be prepared by known processes. Thus phosphonic acid derivatives of formula VIII esterified, for example, with two different biolabile groups can be prepared by first removing one of the two ester groups from the phosphonic acid diesters of formula VIII, in which $R^{101}$ and $R^{201}$ are each the same group, for example lower alkyl, under the action of a base such as an alkali metal hydroxide, for example sodium hydroxide, and then reacting the resulting monoester or its salt with an appropriate compound of formula Va or Vb. To accelerate the reaction, it is possible to add suitable catalysts such as tetra-lower alkylammonium salts, for example tetrabutylammonium hydroxide. Suitable alkali metal halides such as alkali metal iodides, for example sodium iodide, can advantageously be added to the reaction mixture in order to accelerate the course of the reaction. The reaction can be carried out in a dipolar aprotic solvent such as a lower alkyl cyanide, for example acetonitrile, a lower aliphatic ether such as diethyl ether, THF or dioxane, in dimethylformamide (DMF), in dimethyl sulfoxide (DMSO) or in mixtures of these solvents. Suitable temperatures for this are between 0° C. and 80° C., preferably between 5° C. and 40° C. Compounds of formula III are disclosed in published European Patent Application No. EP 733,642, and can be prepared by the methods described therein.

The compounds of formula I and their pharmacologically acceptable salts are distinguished by interesting pharmacological properties. In particular, the substances inhibit endothelin-converting enzyme (ECE) and neutral endopeptidase (NEP) and thus have a particularly favourable activity profile for treating cardiac insufficiency.

In cardiac insufficiency, due to a disease-related reduced output efficiency of the heart, a reflex increase in peripheral vascular resistance occurs. As a result, the heart muscle must begin to pump against an increased afterload. In a vicious cycle, this results in increased strain on the heart and worsens the situation further. The increase in the peripheral resistance is mediated, inter alia, by the vasoactive peptide endothelin. Endothelin is the strongest presently known endogenous vasoconstrictory substance and is formed from the precursor big endothelin with participation of the enzyme ECE.

In the syndrome of cardiac insufficiency, as a result of the decreased cardiac output efficiency and the increase in the peripheral resistance, back-pressure phenomena of the blood occur in the pulmonary circulation and the heart itself. As a result, an increased wall tension of the heart muscle occurs in the area of the auricles and chambers. In such a situation, the heart functions as an endocrine organ and secretes, inter alia, the peptide ANP (atrial natriuretic peptide) into the bloodstream. Due to its marked vasodilatory and natriuretic/diuretic activity, ANP brings about both a reduction in the peripheral resistance and a decrease in the circulating blood volume. The consequence is a marked pre- and afterload decrease. This constitutes an endogenous cardioprotective mechanism. This positive endogenous mechanism is limited in that ANP only has a very short half-life in the plasma. The reason for this is that the hormone is very rapidly broken down by NEP.

As a result of inhibition of the ECE activity, the compounds according to the invention prevent the formation of endothelin and thus counteract an increase in the peripheral resistance, which consequently leads to a relief of the strain on the heart muscle. As a result of inhibition of the NEP activity, the substances according to the invention furthermore lead to higher ANP levels and an increased duration of action of ANP. This leads to a reinforcement of the ANP-mediated endogenous cardioprotective mechanism of action. In particular, the substances have a high effectiveness with respect to reinforcement of the diuretic/natriuretic ANP-induced activities.

NEP is involved not only in the breakdown of ANP but also in the breakdown of endothelin. It follows from this that a pure NEP inhibition in addition to the desired increase in the ANP levels would also lead to an unfavorable increase in the endothelin levels. For this reason, a mixed profile of ECE and NEP inhibition is to be regarded as particularly favorable, since it prevents both the breakdown of the natriuretically/diuretically acting ANP (NEP blockade), and simultaneously inhibits the formation of endothelin (ECE inhibition). As a result, the adverse attendant effect of pure NEP inhibitors (increase in the endothelin levels) no longer comes to bear.

1. Determination of the Minimum Toxic Dose

I.v. maximum doses of 215 mg/kg of the test substances (dissolved in 0.1 N aqueous NaOH solution, whose pH had been adjusted to 7.1) were administered to groups of 10 rats each of 250 g body weight (age 5 to 6 weeks). From the time of administration, the animals were carefully observed for 5 hours for clinically recognizable signs of toxicity. Moreover, they were observed twice daily until one week had passed. After expiry of this week, each individual animal was completely dissected and all organs were examined macroscopically. If death or severe toxic symptoms was observed, increasingly smaller doses were administered to further rats until toxic symptoms no longer occured. The lowest dose which caused death or severe toxic symptoms was determined to be the minimum toxic dose. At the dose of 215 mg/kg i.v., the test substance of Preparation Example 2 showed no significant signs of toxicity.

2. In-vitro Investigation of the NEP Inhibitory Action of the Substances.

In order to demonstrate the inhibitory action of the substances according to the invention on neutral endopeptidase (NEP), the inhibitory action of the substances on the hydrolytic degradation of methionine-encephalin (Met-encephalin) occurring as a result of the enzymatic activity of the NEP was investigated in a standard test in vitro. In this test, the measure of the inhibitory activity of the substances determined was their $IC_{50}$ value. The $IC_{50}$ value of a test substance having enzyme-inhibitory activity is that concentration of the test substance at which 50% of the enzymatic activity of the NEP is blocked.

Test Procedure

To carry out the test, respective 100 μl samples of various incubation solutions comprising 10 ng of purified NEP (E.C. 3.4.24.11) and different amounts of test substance and 20 μl substrate (Met-encephalin) and 50 mM tris buffer (tris (hydroxymethyl)aminomethane/HCl, pH 7.4) were prepared.

Per test substance, six different incubation solutions were prepared using three different test substance concentrations, in each case as duplicate determinations.

In each test, two types of control incubation solutions were also included in the treatment, enzyme controls which contain no test substance, and substrate controls which contain neither enzyme nor test substance.

The incubation solutions were incubated for 30 minutes at 37° C. in a shaking water bath. In the course of this, the enzyme reaction was started after 15 minutes by addition of the substrate (Met-encephalin) and stopped at the end of the incubation period by heating for 5 minutes at 95° C. The stopped incubation solution was then centrifuged at 12,000×g for 3 minutes, and the concentrations of unreacted substrate and of hydrolysis products formed by the enzymatic reaction were determined in the supernatant. For this purpose, samples of the respective supernatants were separated by high-pressure liquid chromatography (HPLC) on hydrophobicized silica gel, and the products of the enzymatic reaction and unreacted substrate were determined photometrically at a wavelength of 205 nm. For the HPLC separation, a separating column (4.6×125 mm) was employed, which contained Nucleosil® C 18, 5μ as reversed-phase separating material. The solvent flow rate was 1.0 ml/min and the column was warmed to 40° C. Eluent A was 5 mM $H_3PO_4$, pH 2.5 and eluent B was acetonitrile+1% 5 mM $H_3PO_4$, pH 2.5.

The $IC_{50}$ value of the test substances was calculated in a known manner from the concentrations of hydrolysis products and unreacted substrate measured in the different samples. In this test, the test substance of Preparation Example 2 showed an $IC_{50}$ value for NEP inhibition of 1.7 nM and thus proved to be a highly potent NEP inhibitor.

3. In-vivo Determination of the Effect of the Substances on Diuresis/Natriuresis in Volume-loaded Rats.

The in-vivo activity was investigated in volume-loaded rats. In this experiment, a high cardiac filling pressure was produced by an infusion of isotonic sodium chloride solution, as a consequence of which ANP release and, as a result, diuresis/natriuresis occurred.

Test Procedure

The experiments were carried out using male Wistar rats having a body weight of 200–400 g. Under neuroleptic analgesia (fentanyl; Hypnorm®, manufacturer Janssen), a catheter was tied into the right femoral vein for the background infusion and the volume loading with isotonic sodium chloride solution. After opening the abdomen, a second catheter was inserted in the bladder and the urethra was tied off so that a measurement of urinary volume, natriuresis and kaliuresis was possible.

The abdomen was closed again, and the animals received a continuous infusion of sodium chloride solution (0.5 ml/100 g of body weight) over the total experimental period of 2 hours. After an equilibration period of 30 minutes, urine samples were collected three times in each case over a period of 10 minutes in a preliminary phase before test substance administration. These preliminary values ("predrug" values) were determined in order to check that a continuous urine flow was taking place in the test animals.

The solutions comprising the test substances were then administered intravenously (bolus injection in the femoral vein) or orally (by means of stomach tube) to groups of 10 rats in each case. For both administration forms, one control animal group in each case received only placebo solutions which contained no active compound. 5 minutes after i.v. administration or 120 minutes after oral administration of the substances, the rats were loaded i.v. with an increased volume of sodium chloride solution (2 ml/100 g of body weight in 2 minutes) and the urine was collected over a period of 60 minutes. The amounts of urine produced in this period were determined, and the sodium and potassium contents contained therein were measured. From the amounts of urine produced, the increase in excretion which took place under volume loading is read off compared with the preliminary values.

In the following Table 1, the increases in urine excretion which have taken place under volume loading after administration of the test substances are indicated in % relative to the urine excretion which has taken place under volume loading after administration of placebo. Furthermore, the amounts of sodium and potassium excreted under volume loading after test substance administration are also indicated in % of the amounts of sodium and potassium excreted under volume loading after administration of placebo. The example numbers in Tables 1 and 2 relate to the subsequent synthesis examples.

TABLE 1

| Test Substance Example No. | Form of Administration Dose in $\mu$mole/kg | Increase in urine excretion under volume loading after administration of test substance in % relative to the urine excretion under volume loading after administration of placebo | Na and K excretion under volume loading amount excreted after administration of test substance in % of the amount excreted after administration of placebo | |
| --- | --- | --- | --- | --- |
| | | | Na | K |
| 2 | 6.0 i.v. | 117 | 147 | 116 |
| | 20.0 i.v. | 149 | 246 | 182 |
| 13 | 30.0 p.o. | 168 | 128 | 87 |
| 22 | 30.0 p.o. | 127 | 161 | 106 |

4. In-vivo Investigations of the ECE Inhibitory Action of the Substances in Rats.

In order to demonstrate the inhibitory action of the substances according to the invention on endothelin-converting enzyme (ECE), the inhibitory action of the substances on the hydrolytic degradation of big endothelin (BIG-ET) to endothelin (ET) taking place as a result of the enzymatic activity of the ECE was investigated in a standard test in vivo. ET is an endogenous strongly vasoconstrictory active substance. An increase in the ET level leads to a blood pressure increase. On infusion of BIG-ET, a blood pressure increase takes place to the extent at which ET is formed from this by ECE-catalysed cleavage. As a measure of the ECE-inhibitory action of the substances, their inhibitory action on the blood pressure increase induced by infusion of BIG-ET was determined.

Test Procedure

The experiments were carried out using male CD® rats from Charles River Wiga having a body weight of 220–280 g. Under ketamine/xylazine anaesthesia, a catheter for substance administration was tied into the left jugular vein and a second for the measurement of the blood pressure was tied into the left carotid artery of the animals. After a recovery time of 30 minutes, the test substance was administered intravenously (i.v.) or intraduodenally (i.d.) to the animals as a solution. After administration of the test substances, the animals each received BIG-ET in a dose of 0.5 nmole/kg intravenously. The period between administration of the test substance and the administration of BIG-ET was 5 minutes in each case on i.v. administration, 15 minutes in each case on i.d. administration of the test substances of Example Nos. 18 and 22, and 30 minutes in each case on i.d. administration of the test substances of Example Nos. 8 and 20. During the next 30 minutes, the systolic and the diastolic blood pressure were recorded every 5 minutes. With untreated animals, the infusion of 0.5 nmol/kg of big endothelin leads reproducibly to a drastic blood pressure increase, which lasts about 30 minutes. The maximum of the blood pressure increase is reached after about 5 minutes.

In the following Table 2, the maximum increase in the blood pressure after BIG-ET administration is indicated for control animals treated with placebo solution and for animals which have been pretreated with the test substance solutions in different doses.

TABLE 2

| Test substance Example No. | Administration form Dose | Blood pressure increase in mm Hg after BIG-ET administration | |
| --- | --- | --- | --- |
| | | systolic pressure | diastolic pressure |
| Control | i.v. | 65 | 32 |
| 2 | 1 mg/kg i.v. | 38 | 23 |
| 2 | 3 mg/kg i.v. | 27 | 14 |
| 2 | 10 mg/kg i.v. | −1 | 0.4 |
| Control | i.d. | 61 | 40 |
| 8 | 30 $\mu$mol/kg i.d. | 25 | 26 |
| 18 | 30 $\mu$mol/kg i.d. | 19 | 17 |
| 20 | 30 $\mu$mol/kg i.d. | 50 | 37 |
| 22 | 30 $\mu$mol/kg i.d. | 36 | 21 |

The above test results show that the compounds of formula I have high affinities for ECE and NEP and counteract the formation of ET and an increase in peripheral vascular resistance and blood pressure induced by this in a dose-dependent manner by inhibition of the ECE activity. The test results also show that the substances additionally contribute to an increase in the ANP level in the blood as a result of inhibition of the ANP-degrading enzyme (NEP) and consequently increase the diuretic/natriuretic effects caused by ANP without causing a significant potassium loss.

Due to their action described above, the compounds of formula I are suitable as medicaments for larger mammals, including man, for the treatment of cardiac insufficiency and for the promotion of diuresis/natriuresis, particularly in patients suffering from cardiac insufficiency. In this connection, compounds of formula I and their salts and biolabile esters are advantageously employed in orally administrable pharmaceutical forms. The doses to be used can differ from individual to individual and vary, of course, depending on the nature of the condition to be treated, the substance used, and the form of administration. In general, however, pharmaceutical forms having an active compound content of 1 to 200 mg per individual dose are suitable for administration to larger mammals, in particular to man.

As medicines, the compounds of formula I can be contained in pharmaceutical preparations, such as, for example, tablets, capsules, suppositories or solutions, with customary pharmaceutical auxiliaries. These pharmaceutical preparations can be prepared by known methods using customary solid or liquid excipients such as, for example, lactose, starch or talc or liquid paraffins and/or using customary pharmaceutical auxiliaries, for example tablet disintegrants, solubilizers or preservatives.

The following examples are intended to illustrate the invention in greater detail, without restricting its scope in any manner.

The structures of the novel compounds were confirmed by spectroscopic investigations, in particular by analysis of the IR spectra and, if appropriate, determination of the optical specific rotations.

EXAMPLE 1

Benzyl (3S)-3-(1-dibenzylphosphonomethylcyclopentane-1-carbonylamino)-2,3,4,5-tetrahydro-2-oxo-1H-1-benzazepine-1-acetate A) 100 ml of dibenzyl phosphite, 12.5 g of paraformaldehyde and 6.2 ml of triethylamine were mixed together with stirring. On slow warming to 55° C., a temperature increase to 120° C. took place. The solution, which was now clear, was allowed to cool to 90° C. and was stirred at this temperature for a further 30 minutes. After cooling to room temperature, it was chromatographed on 1 kg of silica gel at elevated pressure (eluent: n-hexane/ethyl acetate 1:4). After concentrating the fractions and drying the residue in vacuo at 60° C. for 12 hours, 96.1 g of pure, oily dibenzyl hydroxymethylphosphonate were obtained, which was reacted without further purification.

B) 17.8 g of dibenzyl hydroxymethylphosphonate were dissolved in 120 ml of dry dichloromethane. After cooling to −50° C., first 7.3 g of 2,6-lutidine, then 10.6 ml of trifluoromethanesulfonic anhydride were successively added dropwise with exclusion of moisture. The reaction mixture was first stirred at −50° C. for 1 hour, then at 0° C. for 1 hour. For work-up, this mixture was poured onto ice-cold water and the organic phase was first washed with dilute ice-cold hydrochloric acid, then with ice-cold water. After drying of the organic phase over sodium sulfate and filtration, it was evaporated in vacuo. The crude product obtained was chromatographed on 200 g of silica gel (eluent: n-hexane/ethyl acetate 3:2). After concentrating and drying the product fractions, 17.0 g of oily dibenzylphosphonomethyl trifluoromethylsulfonate were obtained.

C) 16.5 ml of diisopropylamine were dissolved in 100 ml of dry THF under a nitrogen atmosphere and with exclusion of moisture and the solution was cooled to −70° C. 65.5 ml of a 1.6 molar solution of n-butyllithium in n-hexane were added dropwise to this mixture. It was then stirred at 0° C. for 30 minutes, cooled to −20° C. and a solution of 5.3 ml of cyclopentanedicarboxylic acid in 20 ml of THF was added dropwise at this temperature. This reaction mixture was first stirred at −20° C. for 30 minutes, then at 0° C. for 2 hours and subsequently cooled to −60° C. A solution of 20.0 g of the product obtained above under B) in 20 ml of THF was slowly added dropwise to this mixture. After addition was complete, it was stirred at −30° C. for 1 hour and then at −20° C. for 1 hour. The reaction mixture was then poured onto ice-cold aqueous potassium hydrogensulfate solution and extracted with methyl tert-butyl ether (=MTBE). The organic phase was separated off, washed with saturated sodium chloride solution, dried over sodium sulfate and, after filtration, concentrated in vacuo. The crude product obtained was purified by chromatography on 300 g of silica gel using pure MTBE to which an amount of methanol continuously increasing from 5% to 10% was admixed. For further purification, the product thus obtained was again chromatographed on 200 g of silica gel, whereby 6.7 g of pure 1-dibenzylphosphonomethyl-1-cyclopentanecarboxylic acid were obtained, m.p.=89–92° C.

D) A solution of 12.65 g of L-(+)-tartaric acid in 54 ml of ethanol heated to 65° C. was added to a solution, heated to 65° C., of 24.5 g of racemic tert-butyl 3-amino-2,3,4,5-tetrahydro-2-oxo-1H-1-benzazepine-1-acetate in 54 ml of ethanol. The reaction mixture was stirred at room temperature for one hour. A solution of 1.72 ml of benzaldehyde in 1.3 ml of ethanol was then added dropwise. The suspension obtained was refluxed at 80° C. for 14 hours and then cooled to room temperature. The resulting crystalline precipitate was filtered off with suction, taken up in 80 ml of ethanol and the mixture was again refluxed for 8 hours. It was then cooled to room temperature and the crystals were filtered off with suction and dried at 50° C. under reduced pressure. 23.6 g of tartrate salt having a melting point of 195 to 196° C. were obtained; $[\alpha]_D^{20}$=−152.0° (c=0.5 in methanol).

E) To liberate the base, 23.6 g of the tartrate salt were cooled to 0° C. with stirring in a mixture of 250 ml of water and 108 ml of dichloromethane and adjusted to pH 9.6 by addition of aqueous ammonia solution. The organic phase was separated off, the aqueous phase was extracted again with 30 ml of dichloromethane and the organic phases were combined, dried over sodium sulfate and concentrated under reduced pressure. The residue which remained was crystallized from MTBE and dried under reduced pressure. 12.2 g of tert-butyl (3S)-3-amino-2,3,4,5-tetrahydro-2-oxo-1H-benzazepine-1-acetate were obtained, m.p.=113°–115° C.; $[\alpha]_D^{20}$=−276.2° (c=0.5 in methanol).

F) 3.6 g of the enantiomerically pure tert-butyl ester obtained above were mixed together with 2.8 g of p-toluenesulfonic acid and 6.9 ml of benzyl alcohol in 60 ml of toluene. This mixture was then boiled in a water separator for 3 hours, the toluene was stripped off in vacuo and the residue which remained was stirred with MTBE. After decanting off the solvent, the residue was taken up in dichloromethane and shaken with ice-cold, dilute aqueous sodium carbonate solution. The aqueous phase was extracted with dichloromethane and the combined organic phases were washed with water. The organic phase was then dried over sodium sulfate and evaporated in vacuo. The residue was crystallized from MTBE and the crystals were dried. 3.2 g of benzyl (3S)-3-amino-2,3,4,5-tetrahydro-2-oxo-1H-benzazepine-1-acetate were obtained, m.p.=113–115° C.; $[\alpha]_D^{20}$=−236.8° (c=0.5 in methanol).

G) 5.8 g of the acid obtained above under C) were taken up in 148 ml of dry dichloromethane. 4.8 g of the product obtained above, 3.7 ml of N-methylmorpholine, 1.84 g of 1-hydroxybenzotriazole and 5.8 g of N-(3-dimethylaminopropyl)-N'-ethylcarbodiimide hydrochloride were added successively with ice-cooling to the solution obtained. The reaction mixture was then stirred at room temperature for 1 hour with exclusion of moisture. For work-up, the reaction mixture was diluted with dichloromethane and washed successively with water, aqueous potassium hydrogensulfate solution, water, aqueous sodium bicarbonate solution and again with water. Drying of the organic phase over sodium sulfate and evaporation in vacuo yielded 10.5 g of crude product, which was purified chromatographically on 200 g of silica gel (eluent: n-hexane/ethyl acetate 3:7). After evaporation of the product fractions and drying in vacuo, 6.5 g of the pure title compound were isolated as a solid foam, IR: 3400, 3310, 2940, 1740, 1650 cm$^{-1}$ (film); $[\alpha]_D^{20}$=−104.6° (c=0.754 in methanol).

EXAMPLE 2

(3S)-3-(1-Phosphonomethylcyclopentane-1-carbonylamino)-2,3,4,5-tetrahydro-2-oxo-1H-1-benzazepine-1-acetic acid A) 1.9 g of benzyl (3S)-3-(1-dibenzylphosphonomethylcyclopentane-1-carbonylamino)-2,3,4,5-tetrahydro-2-oxo-1H-1-benzazepine-1-acetate (preparation see Example 1G) were dissolved in 100 ml of ethanol. 1.2 g of a 5% strength palladium catalyst on active carbon were added to the solution and it was hydrogenated for 3 hours at a hydrogen pressure of 5.5 bar. For workup, the catalyst was filtered out, the filtrate was evaporated in vacuo and the residue was dried. 0.9 g of the title compound was obtained as a foamy product, IR: 3400, 1720, 1630 cm$^{-1}$ (KBr); $[\alpha]_D^{20}$=−140.8° (c=0.5 in methanol).

B) 701 mg of the free acid obtained above and 238 mg of sodium carbonate were dissolved in 60 ml of water and the solution was evaporated in vacuo. The residue obtained was taken up in a little MTBE and again evaporated in vacuo. The solid foam now obtained was crystallized from isopropanol, and the crystals were separated from the solvent and dried in a high vacuum at 60° C. for 2 days. 700 mg of the sodium salt of the title compound were obtained, m.p.>270° C.; $[\alpha]_D^{20}$=−159.7° (c=0.149 in methanol).

EXAMPLE 3

Benzyl (3S)-3-(1-benzylethylphosphonomethylcyclopentane-1-carbonylamino)-2,3,4,5-tetrahydro-2-oxo-1H-1-benzazepine-1-acetate A) A solution of 8.0 g of NaOH in 30 ml of water and 30 ml of ethanol was added dropwise to 27.6 g of diethyl phosphite with ice-cooling and the mixture was stirred at room temperature for 2 hours. It was then concentrated in vacuo and the aqueous residue was extracted 4 times with MTBE. Evaporation of the aqueous phase in vacuo yielded 25.0 g of sodium ethyl hydrogenphosphite as a white powder, which was reacted without further purification.

B) A solution of 4.0 g of NaOH in 22 ml of water was added dropwise with ice-cooling to a solution of 33.9 g of tetrabutylammonium hydrogensulfate in 20 ml of water, the temperature being kept below 25° C. 12.5 g of the product obtained above, dissolved in 15 ml of water, were then added dropwise at room temperature. After stirring for 15 min, the precipitated sodium sulfate was filtered out with suction, and the filtrate was extracted four times with 50 ml portions of dichloromethane each time. The combined organic phases were dried over sodium sulfate and evaporated in vacuo. The residue was dried in vacuo for 1 hour at 40° C., dissolved in 120 ml of anhydrous acetonitrile, and the solution was treated with 7.07 ml of benzyl bromide and 0.4 g of sodium iodide. It was stirred at 50° C. for 12 hours, the solvent was stripped off in vacuo, and the residue was taken up in n-hexane. The solid residue was filtered out with suction, washed with a mixture of n-hexane and MTBE, and the mixture was dried. The resulting solution was evaporated in vacuo, and the residue was chromatographed on 200 g of silica gel (eluent: n-hexane/ethyl acetate 2:3). 6.7 g of benzyl ethyl phosphite were obtained as an oil, IR: 2420, 1255, 970 cm$^{-1}$ (film)

C) 18.0 g of the above product were reacted with 2.5 g of paraformaldehyde and 1.2 ml of triethylamine in the manner indicated in Example 1A). Chromatography on 200 g of silica gel (eluent: ethyl acetate) yielded 16.5 g of benzyl ethyl hydroxymethyl-phosphonate as an oil, IR: 3300, 1230, 1030 cm$^{-1}$ (film).

D) 12.0 g of the product obtained above were reacted with 6.2 g of 2,6-lutidine and 9.0 ml of trifluoromethanesulfonic anhydride in the manner described in Example 1B). Chromatography on 200 g of silica gel (eluent: n-hexane/ethyl acetate 2:3) yielded 16.3 g of oily benzyl-ethylphosphonomethyl trifluoromethylsulfonate, IR: 1410, 1245, 1210, 1010 cm$^{-1}$ (film)

E) The dianion of cyclopentanecarboxylic acid was prepared from 16.08 ml of diisopropylamine, 63.8 ml of 1,6-molar n-butyllithium solution in n-hexane and 5.3 ml of cyclopentanecarboxylic acid according to the method described in Example 1C) and reacted with 16.0 g of the product obtained above under D) in the manner described there. Chromatography of the crude product on 300 g of silica gel (eluent: first n-hexane/ethyl acetate 1:1, which was gradually replaced by pure ethyl acetate) yielded 7.1 g of pure, oily 1-benzylethylphosphonomethyl-1-cyclopentanecarboxylic acid, IR: 2950, 1720, 1210, 1175, 1010 cm$^{-1}$ (film)

F) 3.1 g of the acid obtained above were reacted with 3.2 g of benzyl (3S)-3-amino-2,3,4,5-tetrahydro-2-oxo-1H-1-benzazepine-1-acetate (preparation see Example 1F)), 3.3 ml of N-methylmorpholine, 1.35 g of hydroxybenzotriazole and 3.8 g of N-(3-dimethylaminopropyl)-N'-ethylcarbodiimide hydrochloride according to the method described in Example 1G). Chromatography on 200 g of silica gel (eluent: ethyl acetate) yielded 2.3 g of the title compound as a viscous oil, IR: 3410, 2940, 1735, 1660, 1230, 1020 cm$^{-1}$ (KBr); $[\alpha]_D^{20}$=−121.6° (c=0.495 in methanol)

EXAMPLE 4

Ethyl (3S)-3-(1-benzylethylphosphonomethylcyclopentane-1-carbonylamino)-2,3,4,5-tetrahydro-2-oxo-1H-1-benzazepine-1-acetate A) 5.0 g of tert-butyl (3S)-3-amino-2,3,4,5-tetrahydro-2-oxo-1H-benzazepine-1-acetate (preparation see Example 3E)) and 3.75 g of p-toluenesulfonic acid were boiled in a water separator for 2.5 hours in 80 ml of toluene. A total of 200 ml of ethanol was then added in portions, and the resulting reaction mixture was refluxed for 3.5 hours. The mixture was then concentrated in vacuo, and the residue was taken up with dichloromethane. The mixture was shaken with ice-cold sodium carbonate solution, and the organic phase was washed with water until neutral. The organic phase was dried over sodium sulfate, evaporated in vacuo and the residue which remained was dried. 3.6 g of ethyl (3S)-3-amino-2,3,4,5-tetrahydro-2-oxo-1H-1-benzazepine-1-acetate were obtained, m.p.=106.5°–108° C.; IR: 3350, 3300, 2930, 1735, 1660 cm$^{-1}$ (film); $[\alpha]_D^{20}$=–288.4° (c=0.5 in methanol).

B) 3.1 g of 1-benzylethylphosphonomethyl-1-cyclopentanecarboxylic acid (preparation see Example 3E)) were reacted with 2.6 g of the product obtained above, 3.3 ml of N-methylmorpholine, 1.35 g of hydroxybenzotriazole and 3.8 g of N-(3-dimethylaminopropyl)-N'-ethylcarbodiimide hydrochloride according to the method described in Example 1G). Chromatography on 200 g of silica gel (eluent: first n-hexane/ethyl acetate 1:1, which was changed continuously up to the composition 3:7) yielded 3.7 g of the title compound as an oil, IR: 3410, 2950, 1735, 1660 cm$^{-1}$ (film); $[\alpha]_D^{20}$=–113.6° (c=0.639 in methanol).

EXAMPLE 5

Ethyl (3S)-3-(1-ethylphosphonomethylcyclopentane-1-carbonylamino)-2,3,4,5-tetrahydro-2-oxo-1H-1-benzazepine-1-acetate 3.2 g of ethyl (3S)-3-(1-benzylethylphosphonomethylcyclopentane-1-carbonylamino)-2,3,4,5-tetrahydro-2-oxo-1H-1-benzazepine-1-acetate (preparation see Example 4) were treated with 1.0 g of 5% strength palladium catalyst on active carbon and hydrogenated at a hydrogen pressure of 2.2 bar according to the method described in Example 2. Work-up yielded 2.4 g of the title compound as a foamed resin, IR: 3400, 2950, 1740, 1650 cm$^{-1}$ (KBr); $[\alpha]_D^{20}$=–162.0° (c=0.324 in methanol).

EXAMPLE 6

Ethyl (3S)-3-[1-(pivaloyloxymethylethyl-phosphonomethyl)cyclopentane-1-carbonylamino]-2,3,4,5-tetrahydro-2-oxo-1H-benzazepine-1-acetate 0.6 g of ethyl (3S)-3-(1-ethylphosphonomethyl-cyclopentane-1-carbonylamino)-2,3,4,5-tetrahydro-2-oxo-1H-1-benzazepine-1-acetate (preparation see Example 5) was dissolved in 20 ml of DMF with exclusion of moisture and then treated with 1.86 ml of triethylamine, 0.88 ml of pivaloyloxymethyl chloride and 0.1 g of dimethylaminopyridine. The reaction mixture was stirred overnight, the solvent was evaporated under reduced pressure and the residue was taken up in dichloromethane. The organic phase was washed with water and then dried over sodium sulfate. Concentration in vacuo yielded a crude product which for purification was chromatographed on 50 g of silica gel (eluent: initially n-hexane/ethyl acetate 3:7, the amount of ester gradually being increased to 100%). 188 mg of the title compound were obtained as an oil, IR=1740, 1650 cm$^{-1}$ (CH$_2$Cl$_2$); $[\alpha]_D^{20}$=–124.1° (c=0.228 in methanol).

EXAMPLE 7

Ethyl (3S)-3-[1-(5-indanylethylphosphonomethyl)-cyclopentane-1-carbonylamino]-2,3,4,5-tetrahydro-2-oxo-1H-benzazepine-1-acetate 480 mg of ethyl (3S)-3-(1-ethylphosphono-methylcyclopentane-1-carbonylamino)-2,3,4,5-tetrahydro-2-oxo-1H-1-benzazepine-1-acetate (preparation see Example 5) were dissolved in 10 ml of dry dichloromethane and treated with 0.28 ml of triethylamine. This solution was cooled to –50° C., then 0.09 ml of oxalyl chloride was added. The reaction mixture was then treated at –50°C. with 200 mg of 5-indanol, allowed to warm to 0° C. and stirred at room temperature for a further 5 hours. The organic phase was washed with water, separated off, dried over sodium sulfate and evaporated under reduced pressure. Chromatography on 80 g of silica gel (eluent: n-hexane/ethyl acetate 1:1, the solvent ratio continuously being changed to 1:4) and drying in a high vacuum yielded 220 mg of the title compound as a viscous resin, IR: 1740, 1655 cm$^{-1}$ (CH$_2$Cl$_2$); $[\alpha]_D^{20}$=–135.1° (c=0.205 in methanol).

EXAMPLE 8 tert-Butyl (3S)-3-(1-benzylethylphosphonomethylcyclopentane-1-carbonylamino)-2,3,4,5-tetrahydro-2-oxo-1H-1-benzazepine-1-acetate 5.0 g of 1-benzylethylphosphonomethyl-1-cyclopentanecarboxylic acid (preparation see Example 3E)) were reacted with 5.15 g of tert-butyl (3S)-3-amino-2,3,4,5-tetrahydro-2-oxo-1H-1-benzazepine-1-acetate (preparation see Example 1E)), 4.1 ml of N-methylmorpholine, 2.0 g of hydroxybenzotriazole and 6.3 g of N-(3-dimethylaminopropyl)-N'-ethylcarbodiimide hydrochloride according to the method described in Example 1G). The resulting crude product was chromatographed on 200 g of silica gel (eluent: first n-hexane/ethyl acetate 1:1, then pure ester). 2.6 g of the title compound were obtained as a foamed resin, IR=3410, 3350, 1735, 1655 cm$^{-1}$; $[\alpha]_D^{20}$=–118.1° (c=0.609 in methanol).

EXAMPLE 9

Benzyl (3S)-3-(1-ethylphosphonomethylcyclopentane-1-carbonylamino)-2,3,4,5-tetrahydro-2-oxo-1H-benzazepine-1-acetate A) 3.5 g of 1-benzylethylphosphonomethyl-1-cyclopentanecarboxylic acid (preparation see Example 3E)) were dissolved in 150 ml of ethanol and treated with 1.0 g of 5% strength Pd catalyst on active carbon. The mixture was then hydrogenated at a hydrogen pressure of 2.1 bar for 4 hours. The catalyst was filtered out twice, the filtrate was evaporated in vacuo, and the residue was dried in a high vacuum. 2.60 g of oily 1-ethylphosphonomethyl-1-cyclopentanecarboxylic acid were obtained, which was reacted without further purification.

B) 2.6 g of the product obtained above were dissolved in 100 ml of dry dichloromethane with exclusion of moisture and treated with 3.5 g of carbonyl-diimidazole and 3.569 of benzyl (3S)-3-amino-2,3,4,5-tetrahydro-2-oxo-1H-1-benzazepine-1-acetate (preparation see Example 1F)) and the mixture was stirred overnight. It was then poured onto a saturated aqueous potassium hydrogensulfate solution, and the organic phase was washed with water until neutral and dried over sodium sulfate. The resulting crude product was chromatographed on 150 g of silica gel (eluent: first ethyl acetate, to which dichloromethane was gradually admixed up to a solvent ratio of 1:1). After drying of the product fractions in vacuo, 1.4 g of the title compound were obtained as a solid foam, IR: 3410, 1740, 1645 cm$^{-1}$ (KBr); $[\alpha]_D^{20}$=–130.7° (c=0.339 in methanol).

EXAMPLE 10

Benzyl (3S)-3-(1-diethylphosphonomethyl-1-cyclopentane-1-carbonylamino)-2,3,4,5-tetrahydro-2-oxo-1H-benzazepine-1-acetate A) 69.05 g of diethyl phosphite were reacted with 14.5 g of paraformaldehyde and 6.96 ml of triethylamine analogously to the process described in Example 1A). 66.02 g of diethyl hydroxymethylphosphonate were obtained which, after drying in a high vacuum, was reacted further without additional purification.

B) 21.02 g of the phosphonate obtained above, 15.0 g of 2,6-lutidine and 21.8 ml of trifluoromethane-sulfonic anhydride were reacted in the manner described in Example 1B). 32.5 g of oily diethylphosphonomethyl trifluoromethylsulfonate were obtained.

C) 30.0 g of the trifluoromethylsulfonate obtained above were reacted with 133 ml of a 1.6 molar solution of n-butyllithium in n-hexane and 10.8 ml of cyclopentanecarboxylic acid in the manner described in Example 1C). 11.1 g of diethylphosphonomethyl-1-cyclopentanecarboxylic acid were obtained, IR: 2970, 1730, 1240, 1030 cm$^{-1}$ (film).

D) 5.74 g of the carboxylic acid derivative obtained above were reacted with 7.05 g of benzyl (3S)-3-amino-2,3,4,5-tetrahydro-2-oxo-1H-1-benzazepine-1-acetate (preparation see Example 1F)) according to the method described in Example 1G). The crude product obtained was purified by chromatography on silica gel (eluent: ethyl acetate). 7.95 g of the title compound were obtained, IR=3400, 1745, 1650 cm$^{-1}$ (film); $[\alpha]_D^{20}$=−130.3° (c=0.538 in methanol).

EXAMPLE 11

(3S)-3-(1-Diethylphosphonomethylcyclopentane-1-carbonylamino)-2,3,4,5-tetrahydro-2-oxo-1H-1-benzazepine-1-acetic acid 5.3 g of benzyl (3S)-3-(-diethylphosphonomethyl-1-cyclopentane-1-carbonylamino)-2,3,4,5-tetrahydro-2-oxo-1H-benzazepine-1-acetate (preparation see Example 10) were dissolved in 250 ml of ethanol, treated with 1.5 g of 5% strength Pd catalyst on active carbon and hydrogenated according to the method described in Example 2. 4.3 g of the title compound were obtained, IR=3390, 1730, 1650 cm$^{-1}$ (KBr); $[\alpha]_D^{20}$=−156.6° (c=0.514 in methanol).

EXAMPLE 12

Ethyl (3S)-3-(1-diethylphosphonomethylcyclopentane-1-carbonylamino)-2,3,4,5-tetrahydro-2-oxo-1H-1-benzazepine-1-acetate 2.34 g of (3S)-3-1-diethylphosphonomethylcyclopentane-1-carbonylamino-2,3,4,5-tetrahydro-2-oxo-1H-1-benzazepine-1-acetic acid (preparation see Example 11) were dissolved in dichloromethane with exclusion of moisture, treated with 1.6 ml of N-methylmorpholine, 0.63 g of 1-hydroxybenzotriazole, 2.0 g of N-(3-dimethylaminopropyl)-N'-ethylcarbodiimide hydrochloride and 0.6 ml of ethanol and stirred at room temperature for 4 hours. The reaction mixture was then washed in turn with water, potassium hydrogensulfate solution, water, sodium hydrogencarbonate solution and again with water. The organic phase was then separated, dried over sodium sulfate and evaporated in vacuo. The resulting product was chromatographed on 200 g of silica gel (eluent: initially ethyl acetate, later supplemented by admixture of 5% methanol) and the product fractions were concentrated and dried in vacuo. 1.6 g of the title compound were obtained, IR=3410, 1740, 1650, 1200, 1030 cm$^{-1}$ (film); $[\alpha]_D^{20}$=−126.1° (c=0.584 in methanol).

EXAMPLE 13

Ethyl (3S)-3-(1-phosphonomethylcyclopentane-1-carbonylamino)-2,3,4,5-tetrahydro-2-oxo-1H-1-benzazepine-1-acetate 1.3 g of ethyl (3S)-3-(1-diethylphosphonomethylcyclopentane-1-carbonylamino)-2,3,4,5-tetrahydro-2-oxo-1H-1-benzazepine-1-acetate (preparation see Example 12) were dissolved in 13 ml of dry dichloromethane under a nitrogen atmosphere. 0.5 ml of bromotrimethylsilane and 0.4 ml of triethylamine were added with ice-cooling and the mixture was stirred over night. Excess solvent was stripped off in vacuo, and the residue was stirred in aqueous acetone for 15 minutes. The residue which remained after evaporation of the solvent was taken up in MTBE to which a little dichloromethane had been added and treated with 0.53 g of S-(−)-α-methylbenzylamine. The precipitated solid was recryatallized once from ethanol, the title compound being obtained as the α-methylbenzylammonium salt of m.p.=210–213° C. IR=2940, 1750, 1650, 1200, 1045 cm$^{-1}$ (KBr); $[\alpha]_D^{20}$32 −141.0° (c=0.2 in methanol).

EXAMPLE 14

Benzyl (3S)-3-(1-phosphonomethylcyclopentane-1carbonylamino)-2,3,4,5-tetrahydro-2-oxo-1-benzazepine-1H-1-acetate 3.8 g of benzyl (3S)-3-(1-diethylphosphopnomethyl-1-cyclopentane-1-cyclopentane-1-carbonylamino-2,3,4,5-tetrahydro-2-oxo-1H-1-benzazepine-1-acetate (preparation see Example 10) were dissolved in 10 ml of dichloromethane, treated with 10.3 ml of trifluoroacetic acid with ice-cooling and the mixture was then stirred at room temperature for 18 hours. The solvent was stripped off in vacuo, and the residue which remained was taken up several times with toluene and in each case evaporated again. The resulting crude product was dissolved in dichloromethane and washed 3 times with water, then the organic phase was separated and dried over sodium sulfate and the solvent was evaporated in vacuo. Drying in a high vacuum yielded 3.0 g of the title compound as an oil, IR=3400, 2950, 1745, 1640 cm$^{-1}$ (KBr), $[\alpha]_D^{20}$=−146.50° (c=0.2 in methanol).

EXAMPLE 15

Benzyl (3S)-3-(1-diisopropylphosphonomethylcyclopentane-1-carbonylamino)-2,3,4,5-tetrahydro-2-oxo-1H-1-benzazepine-1-acetate A) 50.0 g of diisopropyl phosphite, 8.5 g of paraformaldehyde and 4.0 ml of triethylamine were reacted according to the method indicated in Example 1A). Chromatography of the crude product on silica gel (eluent: n-hexane/ethyl acetate 1:4) yielded 37.5 g of diisopropyl hydroxymethylphosphonate as an oil, which was reacted further without purification.

B) 19.6 g of the compound obtained above were reacted with 17.4 ml of trifluoromethanesulfonic anhydride and 11.96 g of 2,6-lutidine in the manner described in Example 1B).

Chromatography of the crude product on silica gel (eluent: n-hexane/ethyl acetate 3:7) yielded 27.4 g of diisopropylphosphonomethyl trifluoromethylsulfonate as an oil, IR=2980, 1410, 1205, 1000 cm$^{-1}$ (film).

C) 27.4 g of the compound obtained above, 10.05 ml of cyclopentanecarboxylic acid and 120 ml of a 1.6 molar solution of n-butyllithium in n-hexane were reacted according to the method described in Example 1C). Chromatography of the crude product on silica gel (eluent: first n-hexane/ethyl acetate 3:7, to which increasing amounts of ester up to 100% were added little by little) yielded 10.6 g of diisopropylphosphonomethyl-1-cyclopentanecarboxylic acid of m.p.=53–57° C.

D) 2.05 g of the compound obtained above were reacted with 2.24 g of benzyl (3S)-3-amino-2,3,4,5-tetrahydro-2-oxo-1H-1-benzazepine-1-acetate (preparation see Example 1F)) according to the method described in Example 1G). 3.5 g of the title compound were obtained as an oil, IR=3410, 1735, 1650, 1240, 1180 cm$^{-1}$ (film); $[\alpha]_D^{20}$=−127.5° (c=0.287 in methanol).

EXAMPLE 16

Ethyl (3S)-3-(1-benzylisopropylphosphonomethylcyclopentane-1-carbonylamino)-2,3,4,5-tetrahydro-2-oxo-1H-1-benzazepine-1-acetate A) 92.0 ml of diisopropyl phosphite and 22.2 g of NaOH were reacted in the manner described in Example 3A). 88.0 g of sodium isopropyl hydrogenphosphite were obtained, which was reacted without further purification.

B) 88.0 g of the compound obtained above and 34 ml of benzyl bromide were reacted analogously to the method described in Example 3B). 46.3 g of benzyl isopropyl phosphite were obtained as an oil, which was reacted without further purification.

C) 46.3 g of the compound obtained above were reacted with 6.1 g of paraformaldehyde and 2.87 ml of triethylamine according to the method described in Example 1A). 24.0 g of benzyl isopropyl hydroxymethylphosphonate were obtained as an oil, IR=3300, 1230, 995 cm$^{-1}$ (film).

D) 24.0 g of the compound obtained above were reacted with 18.01 ml of trifluoromethanesulfonic anhydride and 13.57 ml of 2,6-lutidine according to the method described in Example 1B). 32.5 g of benzylisopropylphosphonomethyl trifluoromethylsulfonate were obtained as an oil, IR=2980, 1410, 1245, 1000 cm$^{-1}$ (film).

E) 32.5 g of the compound obtained above, 9.65 ml of cyclopentanecarboxylic acid and 13.4 ml of a 1.6 molar solution of n-butyllithium in n-hexane were reacted according to the method described in Example 1C). Chromatography of the crude product on silica gel (eluent: first n-hexane/ethyl acetate 1:1, then pure ester, then ethyl acetate with 5% by volume of isopropanol) yielded 7.0 g of 1-benzylisopropylphosphonomethyl-1-cyclopentanecarboxylic acid, which was reacted without further purification.

F) 1.25 g of the compound obtained above and 1.06 g of ethyl (3S)-3-amino-2,3,4,5-tetrahydro-2-oxo-1H-1-benzazepine-1-acetate (preparation see Example 4A) were reacted according to the method described in Example 1G). 0.68 g of the title compound was obtained, IR=2400, 1735, 1655, 1200, 985 cm$^{-1}$ (film); $[\alpha]_D^{20}$=−123.0° (c=0.1 in isopropanol).

EXAMPLE 17 tert-Butyl (3S)-3-(1-ethylphosphonomethylcyclopentane-1-carbonylamino)-2,3,4,5-tetrahydro-2-oxo-1H-1-benzazepine-1-acetate 2.2 g of tert-butyl (3S)-3-(1-benzylethylphosphonomethylcyclopentane-1-carbonylamino)-2,3,4,5-tetrahydro-2-oxo-1H-1-benzazepine-1-acetate (preparation see Example 8) were hydrogenated at a hydrogen pressure of 2.5 bar using 1.0 g of a 5% strength Pd catalyst on active carbon according to the method indicated in Example 2. 1.7 g of the title compound were obtained, IR: 3400, 1735, 1650 cm$^{-1}$ (film); $[\alpha]_D^{20}$=−158.2° (c=0.515 in methanol).

EXAMPLE 18 tert-Butyl (3S)-3-[1-(pivaloyloxymethylethylphosphono-methyl)cyclopentane-1-carbonylamino]-2,3,4,5-tetrahydro-2-oxo-1H-benzazepine-1-acetate 0.6 g of tert-butyl (3S)-3-(1-ethylphosphono-methylcyclopentane-1-carbonylamino)-2,3,4,5-tetrahydro-2-oxo-1H-1-benzazepine-1-acetate (preparation see Example 17) were reacted with 1.73 ml of triethylamine, 0.86 ml of pivaloyloxymethyl chloride and 0.1 g of dimethylaminopyridine according to the method indicated in Example 6. After chromatography on silica gel (eluent: ethyl acetate), 392 mg of the title compound were obtained as a viscous resin, IR=1740, 1650 cm$^{-1}$ (CH$_2$Cl$_2$); $[\alpha]_D^{20}$=−122.90° (c=0.257 in methanol).

FOR EXAMPLE 20 tert-Butyl (3S)-3-[1-phosphonomethylcyclopentane-1-carbonylamino)-2,3,4,5-tetrahydro-2-oxo-1H-1-benzazepine-1-acetate: salt forms A) 961 mg of the free phosphonic acid indicated above were mixed with 212 mg of sodium carbonate and 20 ml of water. The resulting mixture was filtered and the filtrate obtained was evaporated in vacuo. The residue obtained was crystallized from ethanol and the crystals were dried at 60° C. in vacuo for one day. 750 mg of sodium salt of the title compound were obtained, m.p.>270°C., $[\alpha]_D^{20}$=−141.5° (c=0.25 in methanol).

B) 961 mg of the free phosphonic acid indicated above were dissolved in 20 ml of MTBE and treated with 0.42 ml of tert-butylamine. The resulting solution was evaporated in vacuo, and the residue obtained was taken up in a mixture of MTBE/n-hexane. The crystals formed in this solvent mixture were separated and dried at 60° C. in vacuo. 950 mg of ammonium salt of the title compound were obtained, m.p.=215°–220° C.; $[\alpha]_D^{20}$=−149.80° (c=0.26 in methanol).

The compounds of formula I listed in the following Table 3 can also be prepared by the processes described in the foregoing examples.

TABLE 3

| Example No. | R$^1$ | R$^2$ | R$^3$ | IR [cm$^{-1}$] | $[\alpha]_D^{20}$ |
|---|---|---|---|---|---|
| 19 | Bn | Bn | $^t$Bu | 3420, 2954, 1742, 1668, 991, (KBr) | −121.3° |
| 20 | H | H | $^t$Bu | 3400, 2970, 1740, 1660, 990 (CH$_2$Cl$_2$) | −166.5° |
| 21 | POM | POM | $^t$Bu | 3360, 2970, 1750, 1660, 1155, 1095 (film) | |
| 22 | Et | H | H | 3380, 1730, 1640, 1040, 980 (KBr) | −156.6° |
| 23 | Ind | Et | Bn | 3400, 1740, 1660 (film) | −117.5° |
| 24 | Ind | Et | H | 3400, 1735, 1650 (KBr) | −139.4° |
| 25 | POM | POM | Bn | 3400, 1745, 1655 (CH$_2$Cl$_2$) | −92.2° |
| 26 | POM | POM | H | 3400, 1745, 1650 (KBr) | −122.6° |
| 27 | Ind | Ind | Bn | | −92.8° |

TABLE 3-continued

| Example No. | R¹ | R² | R³ | IR [cm⁻¹] | $[\alpha]_D^{20}$ |
|---|---|---|---|---|---|
| 28 | Ind | Ind | H | 3400, 1735, 1650 (KBr) | −104.2° |
| 29 | ⁱPr | ⁱPr | H | 3400, 1730, 1650, 1180 (KBr) | −150.6° |
| 30 | ⁱPr | H | Et | 3380, 1740, 1650, 1200, 995 (KBr) | −147.0° |
| 31 | ⁱPr | H | H | 3400, 2955, 1740, 1650 (film) | −152.8° |
| 32 | ⁱPr | Ind | Bn | 3410, 2945, 1745, 1655 (CH₂Cl₂) | −122.0° |
| 33 | ⁱPr | Bn | Bn | 3410, 2950, 1740, 1655 (film) | −119.3° |
| 34 | Et | Et | ᵗBu | 3322, 2974, 1715, 1661, 1159 (film) | −135° |

Et = ethyl; ᵗBu = tert.-butyl; POM = pivaloyloxymethyl; Ind = 5-indanyl; Bn = benzyl; ⁱPr = isopropyl Example I Capsules Comprising tert-butyl (3S)-3-[1-(pivaloyloxymethylethylphosphonomethyl) cyclopentane-1-carbonylamino]-2,3,4,5-tetrahydro-2-oxo-1H-benzazepine-1-acetate Capsules were prepared having the following composition per capsule:

| | |
|---|---|
| tert-Butyl (3S)-3-[1-(pivaloyloxymethyl-ethylphosphonomethyl)cyclopentane-1-carbonylamino]-2,3,4,5-tetrahydro-2-oxo-1H-benzazepine-1-acetate | 20 mg |
| Maize starch | 60 mg |
| Lactose | 301 mg |
| Ethyl acetate | q.s. |

The active compound, the maize starch and the lactose were processed to give a homogeneous pasty mixture with the aid of ethyl acetate. The paste was comminuted and the resulting granules were transferred to a suitable metal plate and dried at 45° C. to remove the solvent. The dried granules were passed through a comminuting machine and mixed in a mixer with the following auxiliaries:

| | |
|---|---|
| Talc | 5 mg |
| Magnesium stearate | 5 mg |
| Maize starch | 9 mg | and then dispensed into capsules each containing 400 mg (=capsule size 0).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A compound corresponding to the formula I

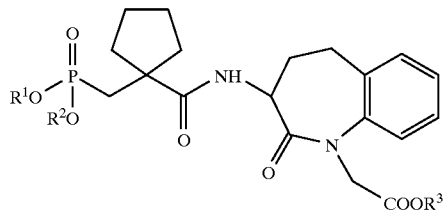

wherein
$R^1$ is hydrogen or a group forming a biolabile phosphonic acid ester,
$R^2$ is hydrogen or a group forming a biolabile phosphonic acid ester and
$R^3$ is hydrogen or a group forming a biolabile carboxylic acid ester
or a physiologically acceptable salt of an acid of formula I.

2. A compound according to claim 1, wherein $R^3$ is hydrogen or lower alkyl.

3. A pharmaceutical composition comprising a pharmacologically active amount of a compound according to claim 1 and at least one pharmaceutical carrier or adjuvant.

4. A process for preparing a compound corresponding to formula I

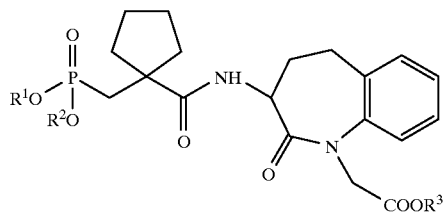

wherein
$R^1$ is hydrogen or a group forming a biolabile phosphonic acid ester,
$R^2$ is hydrogen or a group forming a biolabile phosphonic acid ester, and
$R^3$ is hydrogen or a group forming a biolabile carboxylic acid ester,
or a physiologically acceptable salt of an acid of formula I, said process comprising the steps of:
a) for preparing a compound corresponding to formula IV

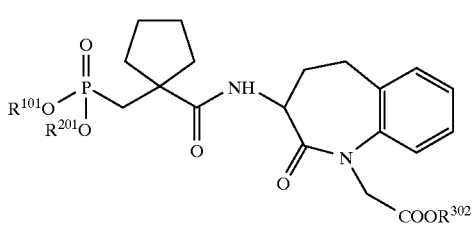

wherein
$R^{101}$ and $R^{201}$ independently of one another are each hydrogen or a phosphonic acid protective group, and
$R^{302}$ is a carboxylic acid protective group, reacting a compound corresponding to formula II

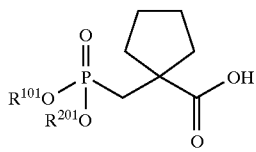

wherein $R^{101}$ and $R^{201}$ have the above meanings, with a compound corresponding to formula III

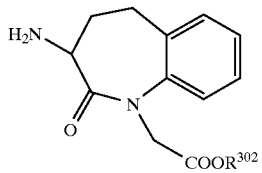

wherein $R^{302}$ has the above meaning, and
if at least one of $R^{101}$ and $R^{201}$ is hydrogen, optionally esterifying the free phosphonic acid function(s) with a compound corresponding to formula Va or formula Vb $$R^{110}\text{-Y} \quad \text{(Va)}$$
$$R^{210}\text{-Y} \quad \text{(Vb)}$$

wherein
$R^{110}$ and $R^{210}$ each repesent a group forming a biolabile phosphonic acid ester, and
Y is hydroxyl or a removable leaving group, to form a biolabile phosphonic acid ester group, and b) if in the compound of formula IV at least one of the protective groups $R^{101}$, $R^{201}$ and $R^{302}$ is not a group which forms a biolabile ester, removing that group to liberate an acid function, and optionally converting the liberated acid function into a biolabile ester groups by esterifying a free phosphonic acid function with a compound of formula Va or Vb or esterifying a free carboxylic acid function with a compound of formula Vc $$R^{310}\text{-Y} \quad \text{(Vc)}$$

wherein
$R^{310}$ is a group forming a biolabile carboxylic acid ester, and
Y has the above meaning,
and, optionally converting an acid of formula I into a physiologically acceptable salt or converting a salt of an acid of formula I into a free acid.

* * * * *